United States Patent [19]

Hrishko et al.

[11] Patent Number: 5,267,575
[45] Date of Patent: Dec. 7, 1993

[54] USER-ACTIVATED VACUUM-ASSISTED CONDOM APPLICATOR

[75] Inventors: Daniel G. Hrishko; Gerald D. O'Brien, both of Las Vegas, Nev.

[73] Assignee: C.A.R.E. of Nevada, Las Vegas, Nev.

[21] Appl. No.: 926,126

[22] Filed: Aug. 5, 1992

[51] Int. Cl.$^5$ ............................ A61F 6/02; A61F 6/04
[52] U.S. Cl. ...................................... 128/842; 128/844
[58] Field of Search ........................ 128/842, 844, 918; 604/330, 347–353; 53/434

[56] References Cited

U.S. PATENT DOCUMENTS

| | | | |
|---|---|---|---|
| 2,567,926 | 9/1951 | Dunkelberger | 128/844 |
| 2,900,779 | 8/1959 | Baxter et al. | |
| 3,431,706 | 3/1969 | Stuck | |
| 4,597,244 | 7/1986 | Pharo | |
| 4,809,483 | 3/1989 | Lovik | |
| 4,809,484 | 3/1989 | Lovik | |
| 4,873,996 | 10/1989 | Maurer | 128/844 |
| 4,875,490 | 10/1989 | Quiroz | 128/842 |
| 4,878,335 | 11/1989 | Hardy | |
| 4,920,983 | 5/1990 | Jimenez | 128/844 |
| 4,961,734 | 10/1990 | Kassman | 128/844 |
| 4,966,166 | 10/1990 | Leffler | 128/844 |
| 4,970,844 | 11/1990 | Domenichiello | |
| 4,974,393 | 12/1990 | Rich et al. | |
| 4,984,582 | 1/1991 | Romaniszyn | 128/844 |
| 5,033,256 | 7/1991 | Rupp | |
| 5,088,267 | 2/1992 | Gee | |
| 5,205,298 | 4/1993 | Hurst | 128/842 |

Primary Examiner—Michael A. Brown
Attorney, Agent, or Firm—Francis J. Bouda

[57] ABSTRACT

A user-activated vacuum-assisted condom applicator is shown which enables the user to apply a standard pre-rolled condom. A tubular receptacle and an egg-shaped applicator are arranged to interact with each other. The applicator is hollow and has a small hole at each end and a groove around the external surface of the fat, central portion. The tubular receptacle has a flared opening at one end and a generally closed other end with a small hole centrally disposed therein, and has an internal diameter larger than an erect penis. The egg-shaped applicator is of a size whereby the external central portion with a groove can rest upon the flared open end of the tubular receptacle without entering the tubular receptacle. In use, a rolled condom, as customarily supplied by the manufacturer, is partially unrolled and placed over one end of the egg-shaped applicator until the enlarged, rubberized ring at the open end of the condom fits into the groove in the central portion of the applicator. Thereupon the applicator with a condom secured thereon is applied to the receptacle in a manner whereby the condom is disposed within the receptacle. The rubber ring of the condom is pulled from the applicator over and around the external portion of the flared ends of the receptacle whereby to hold and seal the condom in the receptacle.

Thereupon the user inflates the condom within the receptacle by blowing through the hole at the exposed end of the applicator until the condom is fully inflated within the receptacle. By manually closing the small opening at the closed end of the receptacle and removing the applicator from the open end of the receptacle, the condom remains fully distended within the receptacle, against the inner wall thereof, and the condom with the receptacle as a carrier, can be placed over the penis. Finally, the small opening of the closed end of the receptacle is uncovered to permit natural atmospheric pressure to enter the receptacle, and the condom is properly applied around the penis. The receptacle is thereafter removed and, with the applicator, ready for reuse with another condom on another occasion.

6 Claims, 2 Drawing Sheets

USER-ACTIVATED VACUUM-ASSISTED CONDOM APPLICATOR

BACKGROUND OF THE INVENTION

The use of condoms as a means for preventing conception or the transmission of diseases is well-known. In more recent times, the spread of autoimmunedeficiency (AIDS) has greatly increased the use of condoms under the initiative of females as well as males. This has increased the desirability of providing means for quickly and effectively applying a condom to a penis, either by the female or the male participant in the sexual act, even under those circumstances where the penis has not yet become fully erect.

Many devices have been shown for providing a condom, unrolling and applying same to a penis, and for means of efficiently and economically marketing and promoting the use of condoms. Most of these devices require mechanical assistance or depend upon manual manipulation, and some of the devices are developed particularly for expanding and testing the condoms at the manufacturer's establishment prior to marketing of same. Such devices are shown in the following U.S. patents:

| Baxter et al | 2,900,779 | 08/25/59 |
| Stuck | 3,431,706 | 03/11/69 |
| Pharo | 4,597,244 | 07/01/86 |
| Lovik | 4,809,483 | 03/07/89 |
| Lovik | 4,809,484 | 03/07/89 |
| Hardy | 4,878,335 | 11/07/89 |
| Domenichiello | 4,970,844 | 11/20/90 |
| Rich et al | 4,974,393 | 12/04/90 |
| Rupp | 5,033,256 | 07/23/91 |
| Gee | 5,088,267 | 02/18/92 |

Because the present invention utilizes the creation of pressure to expand the condom prior to use and vacuum at the time of use (as contrasted to expanding and testing the same in the manufacturer's establishment), the Romaniszyn U.S. Pat. No. 4,984,582 is more relevant than the others. However, in the aforesaid Romaniszyn patent, the condom is expanded within a tubular applicator *at the factory,* and the vacuum which pulls the condom in expanded condition must be maintained throughout the packaging, shipping, selling and prior to use. Furthermore, such a device requires expensive marketing, shipping and packaging materials and, once used, is thereafter discarded. The applicator of the present invention can utilize the standard rolled condoms and can be reused as many times as desired.

SUMMARY OF THE INVENTION

The condom applicator of the present invention is designed to gently apply condoms and includes an egg-shaped applicator and a tubular receptacle. The applicator centers and evenly stretches a condom to put it in the receptacle and is also a hollow mouthpiece through which the user can inflate the condom. A hole in the bottom of the receptacle lets the inside air out as the condom inflates, and once that hole is closed manually by the user, the condom stays inflated within the receptacle. Thereafter, the applicator is removed, and the condom can be examined for leaks and any defects which would make it undesirable in use. Then the receptacle with the condom inside can be slipped over the penis, the small hole in the receptacle unplugged, and the condom deflates snugly and gently around the penis. This makes it inexpensive, easy to apply quickly and sanitarily.

Thus an object of the present invention is to provide a user-activated vacuum-assisted device for expanding a standard rolled condom and applying the condom over a penis which may be fully or only partially erect.

Another object of the present invention is to provide a condom applicator which can be reused many times by the user.

Another object of the present invention is to provide a condom applicator which can be easily applied to her male partner by a female.

With the above and other objects in view, more information and a better understanding of the present invention may be achieved by reference to the following detailed description.

DETAILED DESCRIPTION

For the purpose of illustrating the invention, there is shown in the accompanying drawings a form thereof which is at present preferred, although it is to be understood that the several instrumentalities of which the invention consists can be variously arranged and organized and that the invention is not limited to the precise arrangements and organizations of the instrumentalities as herein shown and described.

In the drawings, wherein like reference characters indicate like parts:

DETAILED DESCRIPTION OF THE PREFERRED EMBODIMENT

Figure 1:
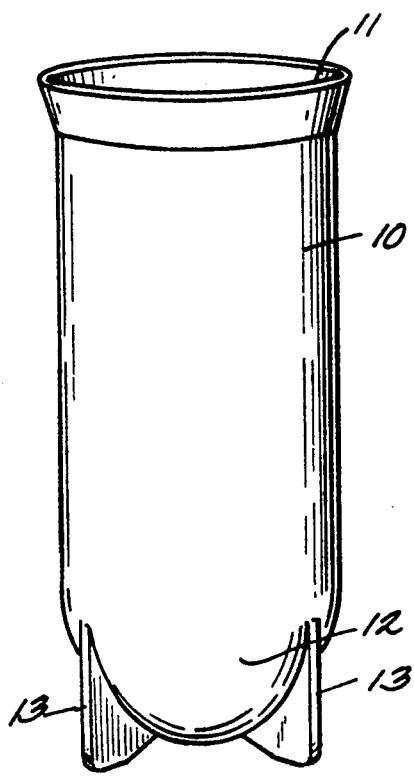
FIG. 1 is an external view of the tubular receptacle of the present invention.
Figure 2:
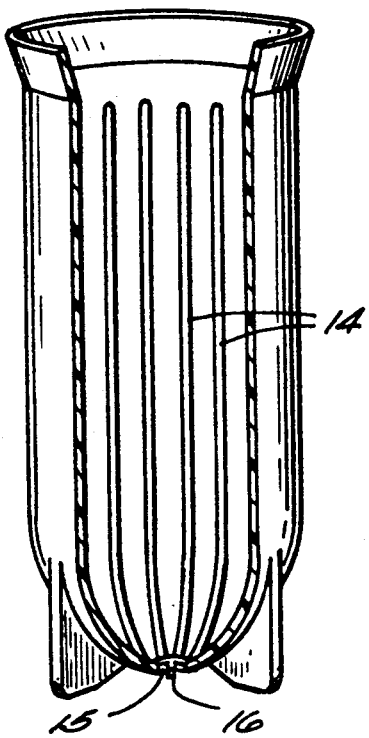
FIG. 2 is a partial fragmentary cross-sectional view of the receptacle of FIG. 1.

Referring now to FIG. 1, there is shown a tubular receptacle (10) having a flared, open, upper-end (11) and a generally rounded closed opposite end (12). The inner diameter of the receptacle is desirably larger than an erect penis and of sufficient length to receive a fully unrolled condom therein.

The receptacle may also have a plurality of feet or supports (13) so that the receptacle may be maintained in an upright position as shown in FIG. 1.

The receptacle also has a plurality of ribs or ridges (14) on the inner wall thereof, which provide structural rigidity and also forms air channels for channeling out any exhaust air when inflating a condom.

Figure 5:
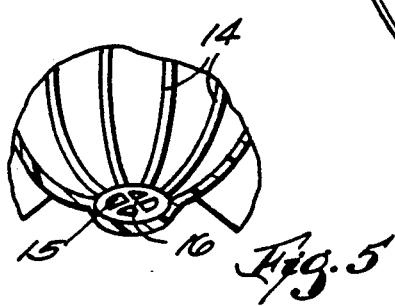
FIG. 5 is an enlarged, sectional view of the portion circled at the bottom of the receptacle shown in FIG. 2.

Additionally, at the rounded, generally closed end (12) of the receptacle, a hole (15) is provided through which air can be exhausted and, furthermore, as shown in FIG. 5, this opening (15) has a cross-bar (16) which prevents an inflated condom from plugging the hole (15).

The open, upper-end (11) is flared outwardly so as to afford better insertion over a penis, and also prevents the condom ring from unrolling back over the tube as will be hereinafter described.

It is to be understood that the construction and materials of the receptacle must be smooth and lightweight, and all parts smoothly rounded so as to lessen the chance of tearing the condom when applied thereto.

Figure 3:
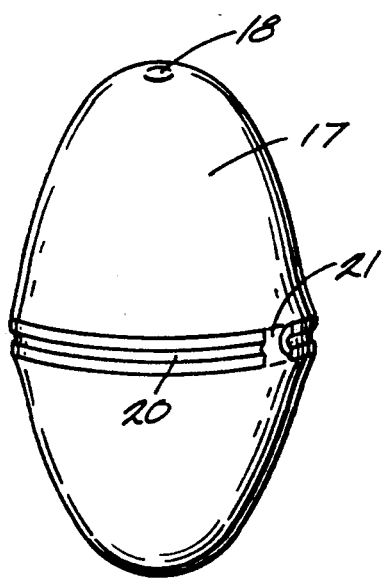
FIG. 3 is an external view of the egg-shaped applicator of the present invention.
Figure 4:
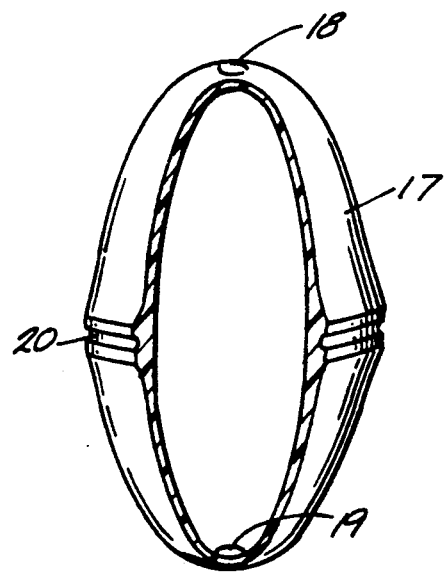
FIG. 4 is a fragmentary, partial, cross-sectional view of the applicator of FIG. 3.

Referring now to FIG. 3, there is shown a generally egg-shaped applicator (17). The applicator is hollow, as shown in FIG. 4, and has a hole (18) at one end and another hole (19) at the opposite end thereof.

Around the central perimeter of the applicator, a groove (20) is formed of such a size as to accept the elastic ring of a standard condom. Furthermore, a small recess or cavity (21) is provided which enables the user easily to grasp the elastic ring of the condom once the condom has been applied over the applicator as will be hereinafter described.

The diameter of the flared opening (11) of the receptacle and the diameter of the enlarged central portion of the applicator are chosen so that the applicator, with a condom applied thereto, will rest upon the flared opening (11) of the receptacle but will not pass into the interior of the receptacle.

DESCRIPTION OF USE

Referring now to FIGS. 6–11 inclusive, one can see how the applicator and the receptacle are used to apply the condom to a penis.

Figure 6:
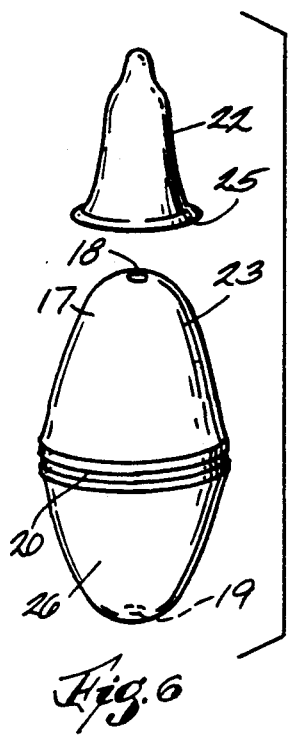
FIG. 6 illustrates how a partially unrolled condom is brought into place around the egg-shaped applicator.
Figure 7:
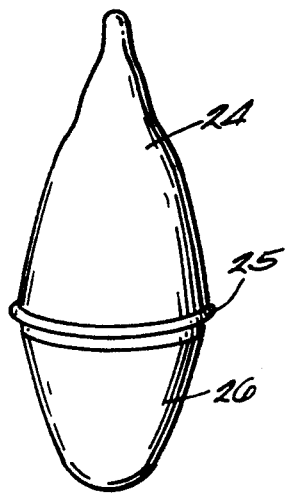
FIG. 7 shows the condom unrolled over the upper portion of the egg-shaped applicator.

In FIG. 6, a partially unrolled condom (22) is brought adjacent the applicator (17) and aligned therewith so that when the condom (22) is placed over one end (23) of the applicator, it can be unrolled as shown at (24) in FIG. 7 until the elastic rubber ring (25) of the condom fits into the groove (20) of the applicator.

Figure 8:
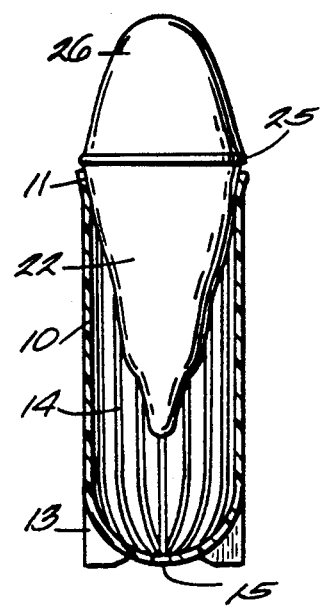
FIG. 8 shows how the egg-shaped applicator is inverted and brought into position at the upper-end of the tubular receptacle.
Figure 9:
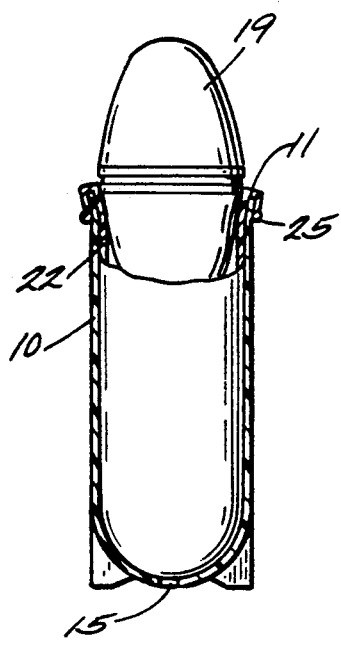
FIG. 9 shows how the ring of the condom is unrolled from the applicator and placed in position around the receptacle, and the condom is inflated within the receptacle.
Figure 10:
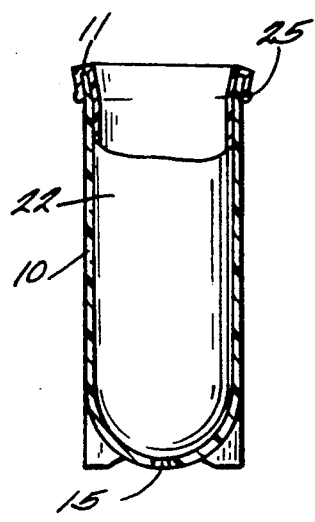
FIG. 10 illustrates how the condom is maintained in inflated position within the receptacle after the applicator is removed.

Thereafter, as shown in FIG. 8, the applicator is inverted so that the end (26) is manually grasped by the user and brought into position above the receptacle (10) so that the condom (22) is disposed within the receptacle beneath the flared end (11). Thereafter, referring to FIG. 9, the elastic ring (25) of the condom is pulled downwardly off the applicator and onto the flared upper end of the receptacle sufficiently far so as to be disposed beneath the flared portion as shown in FIG. 9.

At that point the user inflates the condom within the receptacle by blowing through the opening (19) until the condom is fully distended within the receptacle. Thereafter, the user closes the opening (15) by manually placing one finger over such opening. This prevents any air from entering the receptacle through the opening, and because the upper end is hermetically sealed by the condom ring (25) being wrapped around the flared end, the applicator can then be removed and the condom remains distended within the interior of the receptacle.

While keeping the opening (15) closed by finger contact, the receptacle, with the condom therein, can be gently and easily placed over an erect or semi-erect penis.

Figure 11:
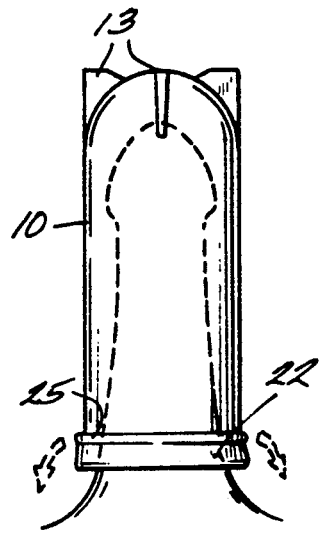
FIG. 11 shows how the receptacle with the inflated condom therein is applied over the penis.

By removing the finger from the opening (15) atmospheric pressure permits air to enter the receptacle through the opening (15), collapsing the condom around the penis. Then the rubber ring (25) of the condom can be unrolled over the flared end of the receptacle as shown in FIG. 11, securely to hold the condom in place on the penis.

The receptacle is then removed and placed to one side along with the applicator, where it is ready for a subsequent reuse.

It is to be understood that the present invention may be embodied in other specific forms without departing from the spirit or special attributes hereof, and it is therefore desired that the present embodiments be considered in all respects as illustrative, and therefore not restrictive, reference being made to the appended claims rather than to the foregoing description to indicate the scope of the invention.

Having thus described my invention, what is claimed as new and desired to protect by Letters Patent are the following:

1. In a user-activated vacuum-assisted condom applicator, a tubular receptacle having an open end and a closed end, with a small aperture in the central portion of the closed end,
    a hollow, egg-shaped applicator with a small hole at each end thereof and a groove in the outer surface of the enlarged central portion thereof,
    the enlarged central portion of said applicator being of such a size as to permit only one-half of the applicator to enter the open end of the tubular receptacle.

2. The applicator of claim 1 wherein the open end of the receptacle is flared outwardly.

3. The applicator of claim 1 wherein the opening at the closed end of the applicator includes means for partially closing said opening.

4. The applicator of claim 1 wherein the interior surface of the cylindrical receptacle includes a plurality of radially-internally-extending ribs.

5. The applicator of claim 1 wherein the external surface of said egg-shaped applicator includes a finger-receiving recess which crosses said groove.

6. The applicator of claim 1 wherein said tubular receptacle includes a plurality of foot-like supports at the closed end thereof to enable the receptacle stand erect on a flat surface.

* * * * *